US007223887B2

(12) United States Patent
Gaucheron et al.

(10) Patent No.: US 7,223,887 B2
(45) Date of Patent: May 29, 2007

(54) MULTIVALENT CATIONIC LIPIDS AND METHODS OF USING SAME IN THE PRODUCTION OF LIPID PARTICLES

(75) Inventors: Jerome Gaucheron, Charray (FR); Kim Wong, Vancouver (CA); Pieter Cullis, Vancouver (CA)

(73) Assignee: The University of British Columbia, Vancouver (CA)

( * ) Notice: Subject to any disclaimer, the term of this patent is extended or adjusted under 35 U.S.C. 154(b) by 513 days.

(21) Appl. No.: 10/323,248

(22) Filed: Dec. 18, 2002

(65) Prior Publication Data

US 2003/0124727 A1    Jul. 3, 2003

Related U.S. Application Data

(60) Provisional application No. 60/341,661, filed on Dec. 18, 2001.

(51) Int. Cl.
*C07C 233/00* (2006.01)
*A61K 9/127* (2006.01)
*A01N 43/04* (2006.01)

(52) U.S. Cl. .................... 564/160; 424/450; 514/44
(58) Field of Classification Search .................... None
See application file for complete search history.

(56) References Cited

U.S. PATENT DOCUMENTS

| 5,785,992 | A |  | 7/1998 | Ansell et al. |
| 5,965,542 | A |  | 10/1999 | Wasan et al. |
| 5,976,567 | A |  | 11/1999 | Wheeler et al. |
| 6,083,497 | A | * | 7/2000 | Huval et al. ............. 424/78.35 |
| 6,320,017 | B1 |  | 11/2001 | Ansell |
| 6,696,424 | B1 | * | 2/2004 | Wheeler ...................... 514/44 |

FOREIGN PATENT DOCUMENTS

WO    WO 00/39241    *    7/2000

OTHER PUBLICATIONS

Rosenzwieg et al (Bioconjugate Chem. 12: 258-263, 2001).*
Schenborn et al (Promega Notes Magazine 52: 2, 1995).*
Promega Technical Bulletin No. 216, retrieved on Jan. 4, 2006 from http://www.promega.com/tbs/tb216/tb216.pdf.*
Fessenden et al (In Organic Chemistry, Willard Grant Press, (1979), pp. 203-209).*
"Synthesis and Properties of Novel Tetraalkyl Cationic Lipids"; J. Gaucheron et al., Journal of Bioconjugate Chemistry, vol. 13, 2002, pp. 671-675.
"Nonviral Vectors in the New Millennium: Delivery Barriers In Gene Transfer", M. Nishikawa et al., Human Gene Therapy, vol. 20, 2001, pp. 861-870.
"Cationic Lipid-DNA Complexes in Gene Delivery: from Biophysics to Biological Applications", M.C. Pedroso de Lima et al., Advanced Drug Delivery Review, vol. 47, pp. 277-294.
"Cationic Lipid Mediated Gene Transfer of CFTR: Safety of a Single Administration to the Nasal Epithelia", M.J. Welsh et al., Human Gene Therapy, vol. 10, 1999, pp. 1559-1572.
"Developments in Liposomal Drug Delivery Systems", N. Maurer et al., Expert Opinions in Biological Therapy, vol. 1, 2001, pp. 1-25.
Lipofection: A Highly Efficient, Lipid-Mediated DNA-Transfection Procedure, P,L. Felgner et al., Proc. Natl. Acad. Sci. U.S.A. vol. 84, 1987, pp. 7413-7417.
"Cationic Liposomes for Gene Therapy", A.D. Miller, Angew. Chem. Int. Ed, vol. 37, 1998, pp. 1768-1785.
"Enhanced Gene Delivery and Mechanism Studies With a Novel Series of Cationic Lipid Formulations", J.H. Felgner et al., Journal of Biol. Chem., vol. 269, 1994, pp. 2550-2561.
"Synthesis and Characterization of Long Chain Alkyl Acyl Carnitine Esters. Potentially Biodegradable Cationic Lipids for use in Gene Delivery", J. Wang et al., Journal of Med. Chemistry, vol. 41, 1998, pp. 2207-2215.
"Synthesis of a Novel Series of Cationic Lipids That Can Act as Efficient Gene Delivery Vehicles Through Systematic Heterocyclic Substitution of Cholesterol Derivatives", H. Gao et al., Gene Therapy, vol. 8, 2001, pp. 855-863.
"Novel Cationic Amphiphilic 1,4-Dihydropyridine Derivatives for DNA Delivery", Z. Hyvonen et al., Biochim Biophys Acta, vol. 1509, 2000, pp. 451-466.
"On the Mechanism Whereby Cationic Lipids Promote Intracellular Delivery of Polynucleic Acids", I.M. Hafez et al., Gene Therapy, vol. 8, 2001, pp. 1188-1196.
"Lipid Polymorphism and the Functional Roles of Lipids in Biological Membranes", P.R. Cullis et al., Biochim Biophys Acta, vol. 559, 1979, pp. 399-420.
"Gene Transfer Mediated by Fusion Protein Hemagglutinin Reconstituted in Cationic Lipid Vesicles", P. Schoen et al., Gene Therapy, vol. 6, 1999, pp. 823-832.

(Continued)

*Primary Examiner*—Richard Schnizer
(74) *Attorney, Agent, or Firm*—Seed IP Law Group PLLC

(57) ABSTRACT

A multivalent cationic lipid having a positively-charged head group including two quaternary amine groups and a hydrophobic portion including four hydrocarbon chains, which may be the same or different and which are optionally substituted alkyl and alkenyl groups, two alkyl chains attached to each of the two quaternary amine groups can be used for the introduction of polyanionic materials such a nucleic acid polymers into cells. Specific cationic lipids are N,N,N',N'-tetraoleyl-N-N'-dimethyl-1,3-propanediammonium chloride and N,N,N',N'-tetraoleyl-N-N'-dimethyl-1,6-hexanediammonium chloride.

21 Claims, 4 Drawing Sheets

OTHER PUBLICATIONS

"Calcium Enhances the Transfection Potency of Plasmid DNA-Cationic Liposome Complexes", A.M. Lam et al., Biochim Biphysica Acta vol. 1463, 2000, pp. 279-290.

"Vesicles of Variable Sized Produced by a Rapid Extrusion Procedure", L.D. Mayer et al., Biochim Biophys Acta, vol. 858, 1986, pp. 161-168.

"The Colorimetric Determination of Phosphorus", C.H. Fiske et al., Journal of Biol. Chem. vol. 66, 1925, pp. 375-379.

"The Role of Dioleoyl Phosphatidylethanolamine in Cationic Liposome Mediated Gene Transfer", H. Farhood et al., Biochim. Biophys. Acta, vol. 1235, 1995, pp. 289-295.

"The Role of Helper Lipids in Cationic Liposome-Mediated Gene Transfer", S.W. Hui et al., Biophysical Journal, vol. 71, 1996, pp. 590-599.

"Stabilized Plasmid-Lipid Particles for Systemic Gene Therapy", Tam P. Monck et al., Gene Therapy, vol. 7, 2000, pp. 1867-1874.

"Stabilized Plasmid-Lipid Particles for Regional Gene Therapy; Formulation and Transfection Properites", Y.P. Zhang et al., Gene Therapy, vol. 6, 1999, pp. 1438-1447.

"Stabilized Plasmid-Lipid Particles: Construction and Characterization", J.J. Wheeler et al., Gene Therapy, vol. 6, 1999, pp. 271-281.

* cited by examiner m = 1 : N,N,N',N'-tetraoelyl-N,N'-dimethyl-1,3-propanediammonium chloride (TODMAC3)

m = 4 : N,N,N',N'-tetraoelyl-N,N'-dimethyl-1,6-hexanediammonium chloride (TODMAC6)

MULTIVALENT CATIONIC LIPIDS AND METHODS OF USING SAME IN THE PRODUCTION OF LIPID PARTICLES

This application claims the benefit of U.S. Provisional Application Ser. No. 60/341,661, filed Dec. 18, 2001, which is incorporated herein by reference.

BACKGROUND OF THE INVENTION

This application relates to a new class of cationic lipids which can be used in lipid particles and in the formation of lipid-nucleic acid complexes for cell transfection.

Monovalent cationic lipids are known in the art, for example as described in U.S. Pat. Nos. 6,320,017; 5,976,567; 5,965,542 and 5,785,992, which are incorporated herein by reference. Plasmid DNA-cationic lipid complexes are the leading non-viral gene therapy vectors used in the clinical setting. (1–4). However, the levels of gene expression that can be achieved using these complexes are substantially lower than can be achieved using viral vectors. Considerable effort has therefore been devoted to synthesizing new cationic lipids that have improved transfection properties over those currently available. (5–10).

SUMMARY OF THE INVENTION

The present invention provides a new class of cationic lipids for use forming nucleic acid complexes for transfection of the nucleic acid. The cationic lipids of the invention are multivalent lipids (generally divalent) of the general formula:

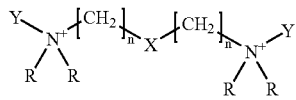

wherein n is an integer 1 or greater, the R groups, which may be the same or different from one another, are optionally substituted alkyl or alkenyl (1 to 4 double bonds) groups of from 1 to 24 carbon atoms, X is $CH_2$, $CH_2CH_2$, NH (in which case the cationic lipid is trivalent), O or S and Y is an alkyl group of from 1 to 6 carbon atoms, a hydroxyalkyl of from 1 to 6 carbon atoms or a hydroxy group. In preferred cationic lipids of the invention, n is from 1 to 2, X is $CH_2$ or $CH_2CH_2$, Y is methyl and the R groups are all the same and are partially unsaturated alkenyl groups.

DETAILED DESCRIPTION OF THE INVENTION

Figure 1:
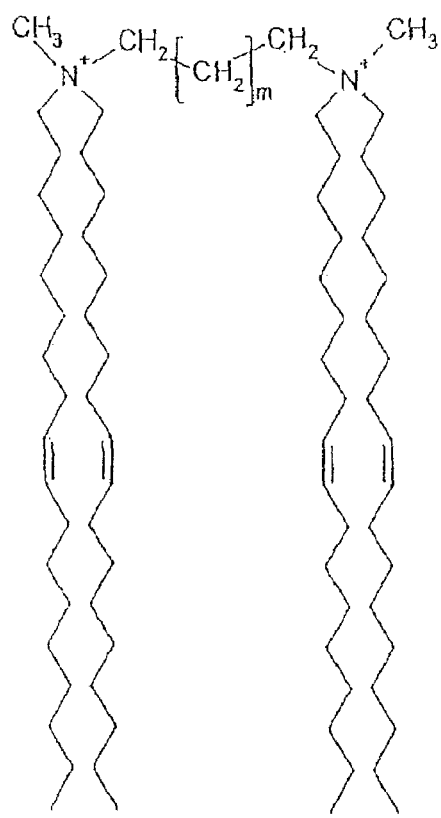
FIG. 1 shows the structures of two multivalent cationic lipids in accordance with the invention.

The present invention provides a new class of cationic lipids for use in forming nucleic acid complexes for transfection of the nucleic acid. This class of compounds, which are referred to herein at times as "catiolipins," contain four hydrocarbon chains and a bridging group linking two ammonium moieties. The bridging group may be all carbon atoms, or it may include hetero atoms. When the bridging group includes a amine nitrogen, the total charge on the cationic lipid is increased.

The catiolipins are multivalent aminolipids, that is they have a net charge of +2 or greater. In specific embodiments, the catiolipins are divalent. The positive charges are the result of two quaternary amine groups linked by the bridging moiety. The positive charge on these quaternary amine groups is independent of pH. If additional nitrogens are incorporated in the bridging moiety, they may be titratable, such that the additional charge is pH dependent, or they may be quaternary amines with pH-independent positive charges.

Catiolipins in accordance with the invention are suitably incorporated into lipid particles containing the catiolipin to promote DNA transfection. The ability of cationic lipids to facilitate intracellular delivery of DNA is related to their ability to induce the non-bilayer hexagonal $H_{||}$ phase in combination with anionic lipids. (11). The catiolipins of the invention have been designed structurally to maximize their ability to induce $H_{||}$ phase organization.

The ability of lipids to adopt the $H_{||}$ phase has been related to their dynamic molecular shape properties. Within this framework, lipids with small cross-sectional area in the headgroup region and a larger acyl chain cross-sectional area exhibit a "cone" shape compatible with $H_{||}$ phase organization. (12). Increasing the cone-shape character of a given lipid can be achieved by increasing the number of alkyl chains associated with the headgroup. Thus, broadly stated, the multivalent cationic lipid of the invention has a positively-charged head group comprising at least two quaternary amine groups and a hydrophobic portion comprising four hydrocarbon chains, which may be the same or different and which are optionally substituted alkyl or alkenyl groups. The cross-sectional size of the headgroup is varied in the catiolipins of the invention by varying the length of the bridge separating the quaternary amines.

The physical properties of catiolipins having a three carbon bridge (TODMAC3) and having a six-carbon bridge (TODMAC6) are quite different. TODMAC6 readily forms bilayer structures, both in the presence and absence of DOPE, on dispersion in an aqueous medium, whereas TODMAC3 does not. Further, when mixed with equimolar (with respect to charge) amounts of DPPS, TODMAC6 forms a homogeneous dispersion that collectively adopts non-bilayer structure in the region of 30° C. TODMAC3 on the other hand is able to interact with only a limited subset of the DPPS, but is able to induce the $H_{||}$ phase for that subset at temperatures as low as 15° C. At higher TODMAC3/DPPS ratios (2:1 on a charge basis)) TODMAC3 is able to induce apparently complete $H_{||}$ organization at temperatures of 25° C. or higher. These results are consistent with steric effects that limit the ability of TODMAC3 to interact with more than one DPPS molecule due to the small size of the TODMAC3 headgroup.

In a specific embodiment, the multivalent cationic lipids of the invention have the formula:

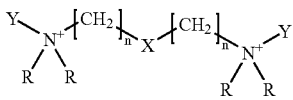

wherein n is an integer 1 or greater for example 1–5, the R groups, which may be the same or different from one another, are optionally substituted alkyl or alkenyl (1 to 4 double bonds) groups of from 1 to 24 carbon atoms, X is $CH_2$, $CH_2CH_2$, NH, O or S and Y is an alkyl group of from 1 to 6 carbon atoms, a hydroxyalkyl of from 1 to 6 carbon atoms or a hydroxy group. In specific preferred embodiments, n is 1 or 2, X is $CH_2$ or $CH_2CH_2$, and/or Y is methyl and the R groups are all the same and are partially unsaturated alkenyl groups. Two specific catiolipins in accordance with the invention are N,N,N',N'-tetraoleyl-N-N'-dimethyl-1,3-propanediammonium chloride and N,N,N',N'-tetraoleyl-N-N'-dimethyl-1,6-hexanedammonium chloride, the structures of which are shown in FIG. 1.

Figure 2:
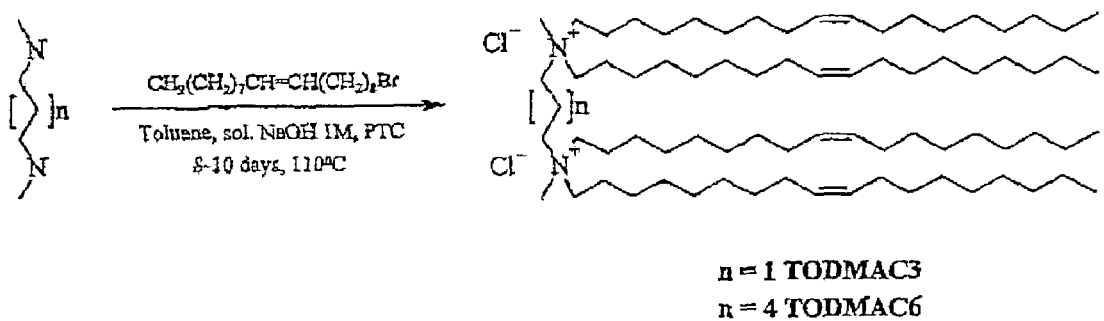
FIG. 2 shows a reaction scheme for synthesis of multivalent cationic lipids in accordance with the invention.

The cationic lipids of the invention can be synthesized by nucleophilic substitution of secondary amines using an alkyl bromide under phase-transfer catalytic condition as outlined in FIG. 2. The strongly basic amines generally require high alkaline reaction conditions so that they remained deprotonated to react with alkyl bromide. Thus, one aspect of the invention is a method for making the catiolipins of the invention comprising the step of reacting a diamine of the general formula:

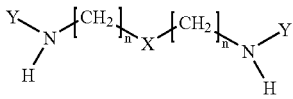

with an alkyl bromide or a mixture of alkyl bromides in a basic phase transfer catalysis reaction medium (toluene, 1 M NaOH), optionally containing t-butyl ammonium hydrogen sulfate. When a mixture of alkyl bromides is used, the product has a random mixture of different alkyl (R) groups dependent on the relative amounts of the alkyl bromides included in the reaction mixture. The reaction is continued under reflux conditions for periods of 1 to 9 days to alkylate the diamine with the alkyl bromide.

The cationic lipids of the invention may be used alone, or they may be formulated with other lipid components to form lipid particles, including liposomes. In addition to the cationic lipids of the invention, the lipid particles may contain neutral lipids or sterols, modified lipids, such as polyamide oligomers or PEG-modified lipids. Such additional components are described in the US patents mentioned above for use in combination with monovalent cationic lipids. For example, as shown in the examples below, the cationic lipids of the invention can be formulated with dioleylphosphatidyl ethanolamine (DOPE) into lipid particles useful for nucleic acid transfection.

The multivalent cationic of the invention may be used in place of or in combination with monovalent cationic lipids for applications known in the art, for example as described in U.S. Pat. Nos. 6,320,017; 5,976,567; 5,965,542 and 5,785,992 mentioned above. Such uses include, without limitation, the introduction of polyanionic materials into cells, both in vivo and in vitro; and as drug delivery compositions for the systemic or local delivery of therapeutic agents or bioactive agents and for use in diagnostic assays.

In a preferred use, the multivalent cationic lipids of the invention are used in the formulation of lipid particles which complex with nucleic acid polymers, which are anionic at physiological pH, and which ate useful for transfection of the nucleic acid polymer into cells. As used in the specification and claims of this application, the term "nucleic acid polymer" refers to any polymeric nucleic acid structure, be it single or double stranded, for which intracellular delivery is desired and encompasses DNA, cDNA, RNA, and mRNA. The term specifically encompasses ribozymes; nucleic acid cloning and/or expression vectors such as plasmids; genetically engineered viral genomes, expression cassettes, and chromosomes from mammalian (especially human) sources. For example, the nucleic acid polymer may be in the form of a plasmid, which includes a genetic sequence to be delivered, as well as promoter and optionally marker elements to confirm transfection and inducer or suicide elements to provide control of the transfected cells after plasmid introduction. Alternatively, the nucleic acid polymer may be a relatively short oligomer, for example having a length of at least 10 nucleotides, which may be useful for genetic immunization, antisense therapy, RNAi therapy or the like.

Transfection is accomplished using standard methods known in the art for transfection with other types of cationic lipid DNA complexes. Since transfection with the multivalent cationic lipids of the invention is generally more efficient, lower levels of lipid-DNA complexes, and shorter times may still provide suitable results.

The invention will now be described with reference to the following, non-limiting examples.

EXAMPLE 1

Synthesis of N,N,N1,N1-Tetraoleyl.N,N'-dimethyl-1,3-propanediammonium Chloride (TODMAC3)

A solution of N,N'-dimethylpropanediamine (0.253 g, 2.5 mmol) and oleylbromide (5 g, 15.1 mmol) in toluene (20 ml) and a solution of tetrabutylammonium hydrogen sulfate (0.4 g, 1.2 mmol) in 1 M sodium hydroxide (20 ml) were stirred under reflux. After 4 days, 2.5 g oleylbromide (7.5 mmol) was added and the reaction continued for another 5 days. The water phase was extracted 2 times with toluene. The combined organic phases were evaporated. The residue was dissolved in $CH_2Cl_2$ and washed six times with 3% hydrochloric acid and three times with saturated aqueous NaCl. The organic phase was evaporated and the remaining material purified by silica gel chromatography ($CH_2Cl_2$/MeOH from 10/0 to 9/1). TODMAC3 was obtained as a pale yellow oil at a yield of 1.15 g (0.98 mmol, 39%). The product was washed six times with 3% hydrochloric acid and three times with saturated aqueous NaCl again.

The cationic lipids were purified by column chromatography using silica gel 60 (Merck, 70–230 mesh) and dichloromethane ($CH_2Cl_2$)/methanol (MeOH) 9/1 mixtures (v/v). The reaction progress was followed by thin layer chromatography (TLC) on silica plates FZ54 (Merck). The following developing systems were used: UV light, $H_2SO_4$/EtOH (1/1 v/v), Dragendorff reagent (Sigma), ninhydrin reagent (Sigma). The observed Rf was 0.43. $^1H$, $^{13}C$, $^{31}P$ NMR spectra were obtained employing a Bruker MSL 200 spectrometer operating at 200.13, 50.3 and 81.02 MHz, respectively. Deuterated chloroform ($CDCl_3$) was used as the solvent in the NMR experiments. Chemical shifts were measured relative to CHCl$_3$ (87.24 ppm) for 1H, and relative to CDCl$_3$ (877.16 ppm) for $^{13}$C. The spectra confirmed to that anticipated for TODMAC3.

EXAMPLE 2

N,N,N',N'-Tetraoleyl-N,N'-dimethyl-1,6-hexanediammonium chloride (TODMAC6) was synthesized using the same procedure as described above in Example 1, substituting N,N'-dimethylhexanediamine for N,N'-dimethylpropanediamine. The product had an observed Rf of 0.61 and an NMR consistent with that expected for the structure.

EXAMPLE 3

As noted above, the ability of cationic lipids to induce the hexagonal H$_\|$ phase in combination with anionic lipids correlates well with their transfection properties in plasmid DNA-cationic lipid complexes. The relative ability of cationic lipids to induce the H$_\|$ phase can be ascertained by measuring the bilayer-to-non-bilayer transition temperature (Tc) of the cationic lipid in equimolar mixtures (with respect to charge) with an anionic phospholipid such as 1,2-dipalmitoyl-sn-glycero-3-[phospho-L-serine] (DPPS). The bilayer-to-non-bilayer transition can be conveniently monitored employing $^{31}$P NMR techniques (12).

To evaluate the polymorphic phase properties of mixtures of TODMAC3 and TODMAC6 with DPPS, lipid mixtures containing 40–50 mg DPPS and appropriate molar ratios of cationic lipids N,N-dioleyl-N-N-dimethylammonium chloride (DODAC), TODMAC3, and TODMAC6 were prepared by drying from chloroform solution, placed in 10 mm NMR tubes and hydrated with 1.5 mL distilled water. Free induction decays (FIDs) corresponding to 1000 scans were obtained by using a 3.0 J.1S 60° pulse with a 1 μs interpulse delay and a spectral width of 25,000 Hz. A gated two-level proton decoupling was used to ensure sufficient decoupling with minimum sample heating. An exponential multiplication corresponding to 50 Hz of line broadening was applied to the FIDs prior to Fourier transformation. The sample temperature (±1° C.) was regulated using a Bruker B-VT1000 variable temperature unit. Chemical shifts were referenced to 85% phosphoric acid as an external standard.

In the first series of experiments the temperature dependent polymorphism of TODMAC6/DPPS mixtures was compared to the behaviour of DODAC/DPPS mixtures. At 25° C. both mixtures exhibited $^{31}$P NMR lineshapes indicative of bilayer structure. However at 30° C. the mixture containing TODMAC6 has largely adopted the H$_\|$ phase or a structure giving rise to a narrow isotropic $^{31}$P NMR peak, whereas the dispersion containing DODAC remained in a bilayer organization at 35° C. On the basis of this behaviour it would be expected that TODMAC6 should exhibit transfection properties that are comparable to or slightly better than DODAC when used in plasmid-DNA-cationic lipid complexes.

Comparable experiments on dispersions of TODMAC3/DPPS (0.5:1 mol:mol) showed that at temperatures as low as 15° C. an H$_\|$ component is clearly visible, however the large bulk of the phospholipid remains in the bilayer organization and the proportion in the H$_\|$ phase does not increase as the temperature is raised. This behaviour is consistent with a limited solubility of the TODMAC3 in the DPPS component in the lipid mixture. This maybe due to steric constraints associated with the need to form ion pairs between the cationic lipid and two DPPS molecules in order to form the H$_\|$ phase. For example, if only one DPPS molecule was able to form an ion pair with each TODMAC3, 50% of the DPPS would be unpaired and thus remain in the bilayer organization. If this is the case it would be expected that TODMAC3/DPPS systems containing higher proportions of TODMAC3 should exhibit increased preference for non-bilayer structure. The phase properties of a mixture containing equimolar proportions of TODMAC3 and DPPS were therefore investigated. This system exhibited an increased preference for H$_\|$ phase structure. On the basis of this behaviour TODMAC3 would not be expected to be as effective a transfection agent as DODAC on a charge for charge basis, but nevertheless should be useful as a transfection agent.

EXAMPLE 4

To prepare large unilamellar vesicles (LUV), mixtures of cationic lipids and DOPE in chloroform were dried under a stream of nitrogen gas and the residual solvent removed under high vacuum for 2 hours. The resulting lipid films were hydrated with distilled water. LUVs were obtained by extruding the lipid dispersions 10 times through two stacked 100-nm pore size polycarbonate filters (Costar Nuclepore polycarbonate membrane, Lipex Biomembranes extruder) (15). Phospholipid concentrations were determined by the inorganic phosphorus assays according to Fiske and Subbarow (16).

EXAMPLE 5

Lipoplexes were prepared in distilled water at pDNA concentrations ranging from 12.5–25 μg pDNA/ml at positive-to-negative charge ratios between 0.5–5. Plasmid DNA was added under vortexing to cationic LUVs (cationic lipid/DOPE 1:1). In the absence of the helper lipid DOPE, lipoplexes were prepared by addition of the cationic lipids from ethanol solutions to an aqueous solution containing the pDNA. The amount of ethanol in these formulations was between 0.4–2.3%. The lipoplexes were incubated at room temperature for 30 min, diluted to a final concentration of 2.5 μg pDNA/ml with serum-free media (Dulbecco's Modified Eaglels Medium, DMEM) and subsequently applied to BHK cells.

EXAMPLE 6

In vitro Transfection of BHK Cells

BHK cells, grown in DMEM supplemented with 10% fetal calf serum (FCS), 100 U/ml of penicillin and 100 μg/ml of streptomycin, were seeded in 96-well plates at a density of 1×10$^4$ cells per well 24 h before transfection. The next day media was removed and replaced with 100 μl of lipoplexes dispersed in serum-free DMEM (0.25 μg pDNA/100 μl), After 4 hr, lipoplexes were replaced with serum-containing DMEM and cells further incubated for 20 h. After that, the culture medium was aspirated, the cells washed twice with 100 μl of PSS and then lysed through addition of 50 μl of lysis buffer (1% Triton X-100 in PBS). Luciferase activity was measured with a Dynex Luminometer (Dynex model ML3000) using the Luciferase Assay Kit from Promega. The total protein concentration per well was determined using the BCA assay from Pierce. Means and standard deviations were calculated from three independent experiments.

Figure 3:
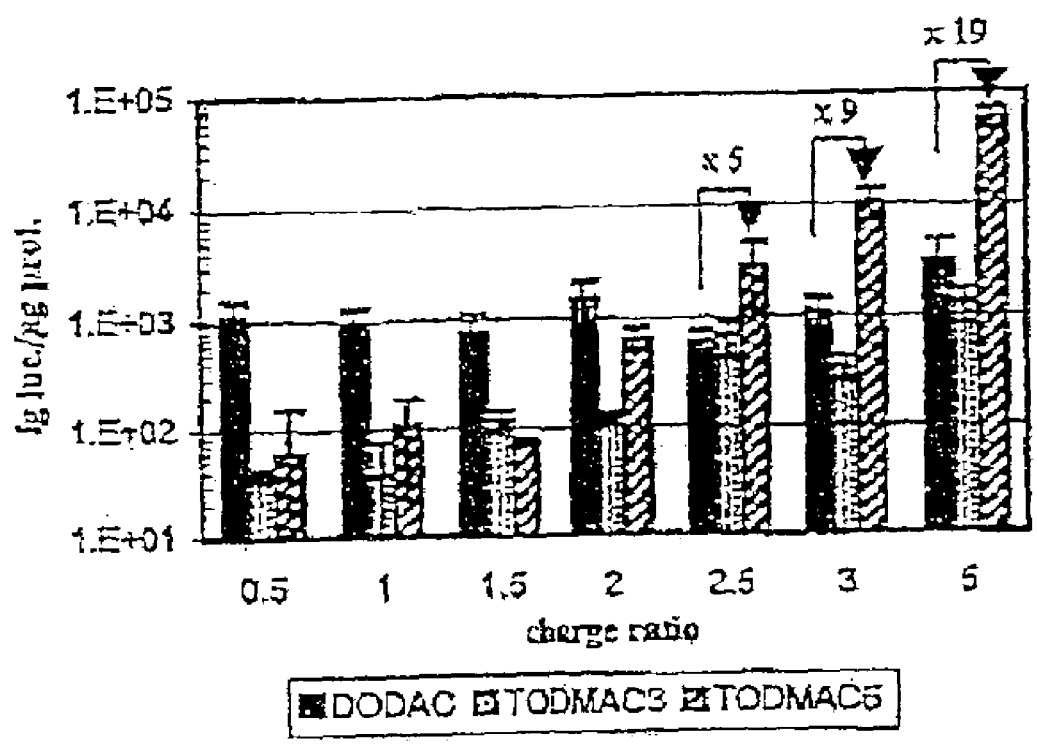
FIG. 3 illustrates the transfection properties of complexes in accordance with the invention.

DNA plasmid complexes containing TODMAC3 and TODMAC6 are usually formed by mixing plasmid DNA with preformed vesicles containing the cationic lipid mixed with equimolar amounts of the- "helper" lipid- dioleoyf-phosphatidylethanolamine (DOPE) (17, 1–8). However it was found that vesicles could not be prepared consisting of TODMAC3/DOPE mixtures, as lipid films prepared of this lipid mixture were extremely difficult to hydrate and formed clumps that could not be extruded. Vesicles of TODMAC6/DOPE could be readily prepared and the transfection properties of complexes formed employing TODMAC6 and DODAC and containing the LO18 plasmid coding for the luciferase gene were tested in vitro using baby hamster kidney (BHK) cells. FIG. 3 illustrates the transfection properties of complexes prepared at cationic lipid-to-DNA charge ratios (positive to negative) ranging from 0.5 to 5. It may be observed that the transfection potency of complexes containing TODMAC6 are comparable to or slightly lower than complexes containing DODAC at charge ratios or two or lower, but are greater at higher charge ratios.

Figure 4:
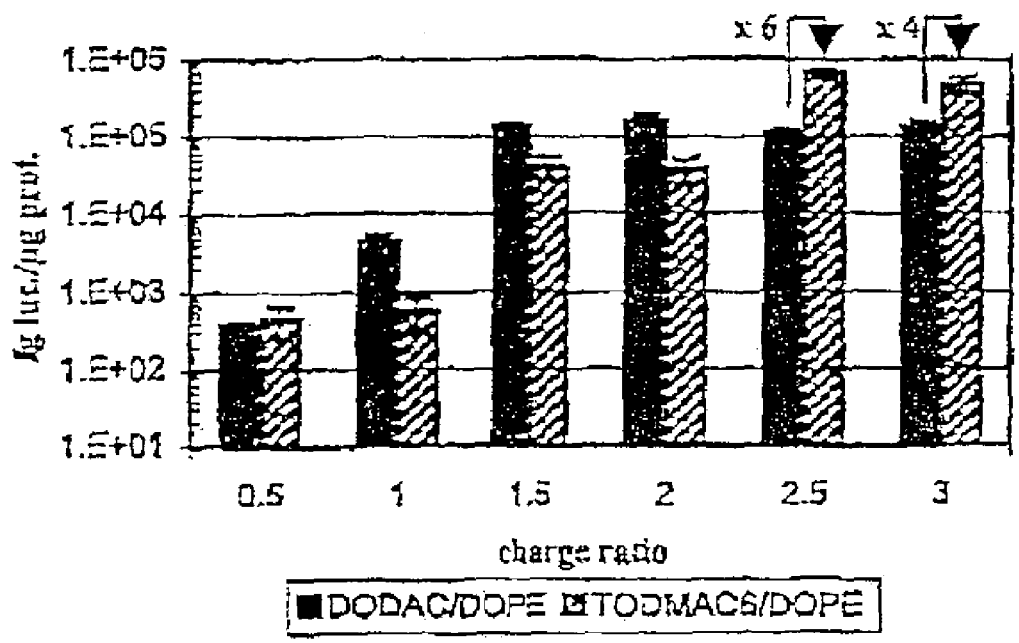
FIG. 4 illustrates the transfection properties of complexes in accordance with the invention.

In order to test the relative transfection potencies of DODAC, TODMAC6 and TODMAC3 a different procedure was used to associate the cationic lipid with the plasmid to form the complexes. In this method the cationic lipid dissolved in ethanol was introduced into an aqueous solution of the plasmid and DOPE was not present. The transfection properties of complexes formed in this manner are shown in FIG. 4. It may be noted that at charge ratios of two and lower DODAC exhibits superior tranfection properties, however at charge ratios above two TODMAC6 exhibits transfection properties that are superior to both DODAC and TODMAC3. Specifically, for charge ratios~2.5, TODMAC6 complexes gave rise to luciferase expression levels 5–20 fold higher than could be achieved with DODAC or TODMAC3.

The following reference are cited herein and are incorporated herein by reference.

REFERENCES (1) Nishikawa M., and Huang L. (2001) Nonviral vectors in the new millennium: delivery barriers in gene transfer. *Hum Gene Ther* 20, 861–70.
(2) Pedroso de Lima M. C., Simoes S., Pires P., Faneca H., and Duzgunes N. (2001) Cationic lipid-DNA complexes in gene delivery: from biophysics to biological applications *Adv Drug Deliv Rev* 47, 277–94.
(3) Welsh M. J., and Zabner J. (1999) Cationic lipid mediated gene transfer of CFTR: safety of a single administration to the nasal epithelia. *Hum Gene Ther* 10, 1559–72.
(4) Maurer N., Fenske D. B., and Cullis P. R. (2001) Developments in liposomal drug delivery systems. *Expert Opin. Biol. Ther* 1, 1–25.
(5) Felgner, P. L., Gadek, T. R., Holm, M., Roman, R., Chan, H. W., Wenz, M., Northrop, J. P., Ringold, G. M., and Danielsen, M. (1987) Lipofection: a highly efficient, lipid-mediated DNA-transfection procedure. *Proc. Natl. Acad. Sci. U.S.A.* 84, 7413–7417.
(6) Miller, A. D. (1998) Cationic Liposomes for gene therapy. *Angew. Chem. Int. Ed.* 37, 1768–1785.
(7) Felgner, J. H., Kumar, R., Sridhar, C. N., Wheeler, C. J., Tsai, Y. J., Border, R., Ramsey, P., Martin, M., and Felgner, P. L. (1994) Enhanced gene delivery and mechanism studies with a novel series of cationic lipid formulations. *J. Biol. Chem.* 269, 2550–2561.
(8) Wang, J., Guo, X., Xu, Y., Barron, L., and Szoka, F. S., Jr. (1998) Synthesis and characterization of long chain alkyl acyl carnitine esters. Potentially biodegradable cationic lipids for use in gene delivery. *J. Med. Chem.* 41, 2207–2215.
(9) Gao H., and Hui K. M. (2001) Synthesis of a novel series of cationic lipids that can act as efficient gene delivery vehicles through systematic heterocyclic substitution of cholesterol derivatives. *Gene Ther* 8, 855–63.
(10) Hyvonen Z., Plotniece A., Reine I., Chekavichus B., Duburs G., and Urtti A. (2000) Novel cationic amphiphilic 1,4-dihydropyridine derivatives for DNA delivery. *Biochim Biophys Acta* 1509, 451–66.
(11) Hafez I. M., Maurer N., and Cullis P. R. (2001) On the mechanism whereby cationic lipids promote intracellular delivery of polynucleic acids. *Gene Ther* 8, 1188–96.
(12) Cullis P R, and de Kruijff B. (1979) Lipid polymorphism and the functional roles of lipids in biological membranes. *Biochim Biophys Acta* 559, 399–420.
(13) Schoen P., Chonn A., Cullis P. R., Wilschut J., and Scherrer P. (1999) Gene transfer mediated by fusion protein hemagglutinin reconstituted in cationic lipid vesicles. *Gene Ther* 6, 823–32.
(14) Lam A. M., and Cullis P. R. (2000) Calcium enhances the transfection potency of plasmid DNA-cationic liposome complexes. *Biochim Biophys Acta* 1463, 279–90.
(15) Mayer L. D., Hope M. J., and Cullis P. R. (1986) Vesicles of variable sizes produced by a rapid extrusion procedure. *Biochim Biophys Acta.* 858, 161–8.
(16) Fiske C. H., Subbarow Y. (1925) The calorimetric determination of phosphorus, *J. Biol. Chem.* 66, 375–379.
(17) Farhood, H., Serbina, N., and Huang, L. (1995) The role of dioleoyl phosphatidylethanolamine in cationic liposome mediated gene transfer. *Biochim. Biophys. Acta* 1235, 289–295.
(18) Hui, S. W., Langner, M., Zhao, Y., Ross, P., Hurley, E., and Chan, K. (1996) The role of helper lipids in cationic liposome-mediated gene transfer. *Biophysical Journal* 71, 590–599.
(19) Tam P., Monck M., Lee D., Ludkovski O., Leng E. C., Clow K., Stark H., Scherrer P., Graham R. W., and Cullis P. R. (2000) Stabilized plasmid-lipid particles for systemic gene therapy. *Gene Ther* 7, 1867–74.
(20) Zhang Y. P., Sekirov L., Saravolac E. G., Wheeler J. J., Tardi P., Clow K., Leng E., Sun P., Cullis P. R., and Scherrer P. (1999) Stabilized plasmid-lipid particles for regional gene therapy: formulation and transfection properties. *Gene Ther* 6, 1438–47.
(21) Wheeler J. J., Palmer L., Ossanlou M., MacLachlan I., Graham R. W., Zhang Y. P., Hope M. J., Scherrer P., and Cullis P. R. (1999) Stabilized plasmid-lipid particles: construction and characterization. *Gene Ther* 6, 271–81.

The invention claimed is:

1. N,N,N',N'-tetraoleyl-N-N'-dimethyl-1,6-hexanediammonim chloride.

2. A method for making N,N,N',N'-tetraoleyl-N-N'-dimethyl-1,6-hexanediammonium chloride comprising the step of reacting N,N'-dimethylhexanediamine with an alkyl bromide or a mixture of alkyl bromides in a basic phase transfer catalysis reaction medium and continuing the reaction under reflux conditions for a period of time sufficient to produce N,N,N',N'-tetraoleyl-N-N'-dimethyl-1,6-hexanediammonium chloride.

3. The method of claim 2, wherein the reaction is continued for a period of 1 to 9 days.

4. The method of claim 2, wherein the reaction medium comprises toluene and 1 M NaOH.

5. The method of claim 4, wherein the reaction medium further comprises t-butyl ammonium hydrogen sulfate.

6. A lipid particle comprising N,N,N',N'-tetraoleyl-N-N'-dimethyl-1,6-hexanediammonium chloride.

7. The lipid particle of claim 6, further comprising one or more additional lipids.

8. A lipid-nucleic acid polymer complex, comprising a nucleic acid polymer complexed with N,N,N',N'-tetraoleyl-N-N'-dimethyl-1,6-hexanediammonium chloride.

9. The lipid-nucleic acid polymer complex of claim 8, wherein said nucleic acid polymer is double-stranded.

10. The lipid-nucleic acid polymer complex of claim 9, wherein said double-stranded nucleic acid polymer is a plasmid.

11. The lipid-nucleic acid polymer complex of claim 9, wherein said double-stranded nucleic acid polymer is DNA.

12. The lipid-nucleic acid polymer complex of claim 9, wherein said double-stranded nucleic acid polymer is RNA.

13. The lipid-nucleic acid polymer complex of claim 8, wherein said nucleic acid polymer is single-stranded.

14. The lipid nucleic acid polymer complex of claim 8, wherein said nucleic acid polymer is an oligomer comprising at least 10 nucleotides.

15. A formulation comprising a nucleic acid polymer and a lipid particle comprising N,N,N',N'-tetraoleyl-N-N'-dimethyl-1,6-hexanediammonium chloride.

16. The formulation of claim 15, wherein said nucleic acid polymer is double-stranded.

17. The formulation of claim 16, wherein said double-stranded nucleic acid polymer is a plasmid.

18. The formulation of claim 16, wherein said double-stranded nucleic acid polymer is DNA.

19. The formulation of claim 16, wherein said double-stranded nucleic acid polymer is RNA.

20. The formulation of claim 16, wherein said nucleic acid polymer is single-stranded.

21. The formulation of claim 15, wherein said nucleic acid polymer is an oligomer comprising at least 10 nucleotides.

\* \* \* \* \*

UNITED STATES PATENT AND TRADEMARK OFFICE
CERTIFICATE OF CORRECTION

PATENT NO.        : 7,223,887 B2
APPLICATION NO. : 10/323248
DATED             : May 29, 2007
INVENTOR(S)       : Jerome Gaucheron et al.

It is certified that error appears in the above-identified patent and that said Letters Patent is hereby corrected as shown below:

Column 8
Lines 57-58, "N,N,N',N'-tetraoleyl-N-N'-dimethyl-1,6-hexanediammonim chloride" should read as --N,N,N',N'-tetraoleyl-N-N'-dimethyl-1,6-hexanediammonium chloride--.

Signed and Sealed this

Twelfth Day of August, 2008

JON W. DUDAS
*Director of the United States Patent and Trademark Office*